United States Patent [19]

Leichnitz et al.

[11] 4,254,657

[45] Mar. 10, 1981

[54] GAS DETECTOR AND METER EMPLOYING INDICATOR TUBES

[75] Inventors: Kurt Leichnitz, Gross Grönau; Peter Naumann, Stockelsdorf, both of Fed. Rep. of Germany

[73] Assignee: Drägerwerk Aktiengesellschaft, Fed. Rep. of Germany

[21] Appl. No.: 41,805

[22] Filed: May 23, 1979

[30] Foreign Application Priority Data

May 29, 1978 [DE] Fed. Rep. of Germany ....... 2823315

[51] Int. Cl.³ .............................................. G01N 1/24
[52] U.S. Cl. ............................................... 73/421.5 R
[58] Field of Search .................. 73/23, 421.5 R, 1 G, 73/3; 422/86, 110

[56] References Cited

U.S. PATENT DOCUMENTS

| | | | |
|---|---|---|---|
| 3,782,198 | 1/1974 | Wächter et al. ................. | 73/421.5 R |
| 3,953,152 | 4/1976 | Sipin ............................. | 73/421.5 R |
| 3,956,940 | 5/1976 | Guild ............................. | 73/421.5 R |
| 4,021,201 | 5/1977 | Vautrain et al. ................. | 422/110 |

Primary Examiner—Stephen A. Kreitman
Attorney, Agent, or Firm—McGlew and Tuttle

[57] ABSTRACT

A gas detecting and measuring device with which the gas or air to be examined is taken into a testing or measuring vessel such as an indicator tube by means of a feed system comprises an electrical motor driven suction pump and a pressure gauge connected thereto for pumping the gas to be tested through a connecting line. The connecting line includes the suction pump and a volume sensor provided in addition to a pressure sensor. The differential signal formed of the volume signal is converted in a characteristic generator to a desired pressure signal and the actual pressure signal from the pressure sensor is applied to a speed governor for the suction pump motor so that the suction pump is controlled to effect equalizing the actual pressure signal with a desired pressure signal.

7 Claims, 2 Drawing Figures

GAS DETECTOR AND METER EMPLOYING INDICATOR TUBES

DESCRIPTION OF THE PRIOR ART

To prove the presence and/or to measure foreign components in gases or air, gas detecting and measuring devices are used. In one group of such gas detecting devices, the gas or air to be examined is directed through an indicator tube containing a detection reagent for the respective component to be determined, the detecting reaction resulting in a coloration. The air or gas to be examined is taken into and directed through the indicator tube by means of manually or mechanically operated pumps. Bellows, diaphragm or piston pumps are used for this purpose. With the pump capacity known and depending on the type of the pump, the air or gas amount needed for the measurement results from the number of strokes or the pumping time.

With the known manually operated bellows pump, up to about 15 pump strokes are to be performed, and the following measurement takes several minutes. With larger amounts of air to be tested, a manual operation is no longer practical. This also applies to measurements in which a definite air amount is to be directed through the indicator tube, in intervals distributed over a longer time period. For such a measurement, known mechanically operated pumps are used.

The time and speed characteristic of a volume to be taken through the indicator tube by suction during the measuring operation depends on the construction of the pump. This "suction characteristic" produces its effect on the indicating response of the indicator tube used with the pump.

In general, indicator tubes are calibrated by using a manually operated pump having definite properties, for example, a bellows pump. Then, to aboid systematic measuring errors, this type of pump must also be used during the measurement proper.

There are known indicator tubes which are used with two different gas feed devices having different suction characteristics. Because of the mentioned affect on the indicating response, these tubes are provided with two different scales corresponding to the two different types of pumping devices. This has the disadvantage that dangerous errors in reading may occur during the measuring operations, due to a mistaken scale. To be able to employ tubes having a single scale, the mechanically operated pump should have a suction characteristic corresponding to that of the manually operated bellows pump which has been used for calibration.

A prior art gas detector to be used with indicator tubes and with which continuous measurement can be performed, employs a movable bellows part such as known from the manually operated pump, to direct the volume by suction through the indicator tube. This bellows part is provided within the range of action of a thrust member which is reciprocated by a drive mechanism, such as clockwork, an electric motor, or the like. The speed of the drive mechanism exceeds that of the movable bellows part during the working stroke, that is, during the expansion caused by the springs. The drive mechanism is controlled in such a way that in each cycle, the thrust member is moved back and forth through a full stroke and then, during the working stroke of the bellows part, stands still in its end position not disturbing the bellows. To control the drive mechanism, a pressure measuring member, such as a pressure pickup, may be connected to the suction side of the bellows part, by which, with an underpressure at the bellows suction side, the drive mechanism is switched off, and is switched on at a normal pressure. In another design, a break contact, controlled by a pressure pickup provided at the suction side of the bellows part, may be connected in the electrical drive circuit of the drive mechanism, which contact is open at underpressure and closed at normal pressure. This prior art gas detector exhibits the suction characteristic of the manually operated bellows pump. However, the mechanical equipment with reciprocating members needed for the drive is very bulky and requires continual checking to insure its operation. The device is voluminous and heavy and, therefore, hardly suitable for being used a different locations (German Pat. No. 1,598,332).

Another known gas or dust detecting and measuring device substantially comprises a low-pressure chamber to which a vacuum pump is connected through a reversing valve and which has a connecting socket for the indicator tube. The low-pressure chamber is further connected to two pressure switches which form part of a circuit including a switching device incorporated in the reversing valve and are connected in such a manner that as soon as the pressure in the low-pressure chamber drops below a predetermined value, adjusted by means of one of the pressure switches, for example, to 540 torr, the reversing valve is switched to connect the circuit with the indicator tube to the low-pressure chamber, while the connection established prior to that between the low pressure chamber and the vacuum pump is shut off. If now tested air is taken in through the indicator tube, the pressure in the low-pressure chamber rises. The other pressure switch which, for example, may be set to 740 torr, switches over as soon as this pressure is attained, so that a connection between the low-pressure chamber and the vacuum pump is established again and the connection between the indicator tube and the low-pressure chamber is interrupted.

What is disadvantageous in this otherwise fully automatically operating gas detector is that while producing the underpressure in the low-pressure chamber, recurrently needed for directing the gas through the tube, dead time periods are obtained in the indicator tube during which no tested air flows therethrough. Since diffusion phenomena depend on time, such as interruption between reaction cycles may change the indication (German Pat. No. 2,141,496).

SUMMARY OF THE INVENTION

The invention is directed to a gas detecting and measuring device employing indicator tubes and performing individual as well as continuous measurements, having a suction characteristic corresponding to that of the known manually operated bellows pump, and being simple in design and easy to handle in reliable operation.

Accordingly it is an objection of the invention to provide a method of insuring reproducible results in measuring gas characteristics by passing the gas through a detection tube or similar container containing a measuring substance and which includes feeding the gas through the tube by pump while sensing both the volume being moved through the tube and the pressure in the tube, converting the volume sensed to a desired pressure signal and applying it plus an actual pressure signal to a subtractor and then to a governor in order to equalize the actual pressure with the desired pressure.

A further object of the invention is to provide a gas detection and measuring device which includes a measuring vessel having a passage therethrough for the gas to be tested with feed means for feeding the gas through said passage which comprises an electrical motor driven suction pump having a speed governor which is arranged to discharge through a connecting line to the passage and which includes a volume sensor in the connecting line as well as a pressure sensor with control means connected to the sensors to convert the volume from a pressure signal to a desired pressure signal and to apply the actual pressure signal to a governor to control the pump so as to equalize the actual pressure with the desired pressure.

A further object of the invention is to provide a gas detection device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

GENERAL DESCRIPTION OF THE PREFERRED EMBODIMENTS

Figure 1:
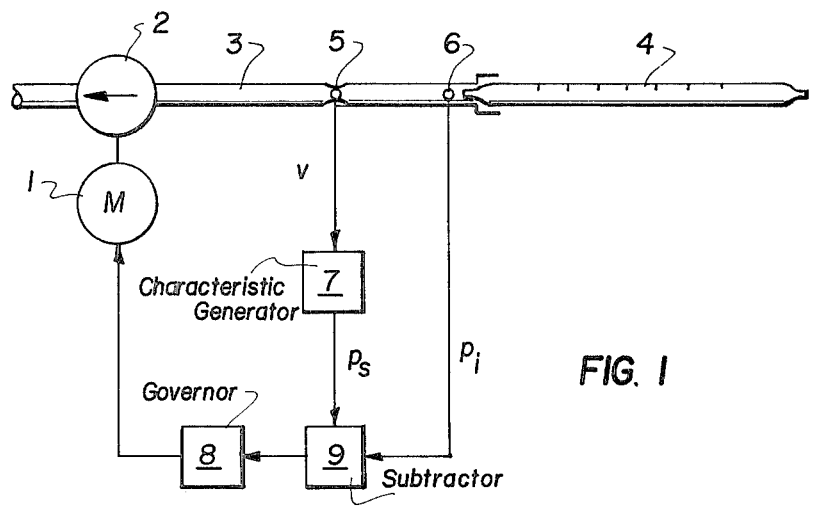
FIG. 1 is a schematic diagram of a gas detection and measuring device constructed in accordance with the invention.

Referring to the drawings in particular, the invention embodied therein comprises a gas detection and measuring device which includes a measuring vessel or tube 4 having a passage therethrough for the passage of the gas to be tested and which also includes feed means associated with the tube including a motor 1 driving a pump 2. The device is capable of performing individual as well as continuous measurements and the pump has suction characteristics corresponding to that of the known manually operated bellows pump and is simple in design and easy to handle and is reliable in operation.

The basic advantages obtained with this solution are that the inventive gas detecting measuring device, including a control built up of conventional electronic elements, makes it possible to reliably reproduce the suction characteristic of the manually operated bellows pump used during the calibration. The construction of this control is simple as its operation remains unchanged even after long periods of service, since no mechanical parts are provided. The use of conventional electronic means permits a series production of gas detectors in which always identical apparatus characteristics are obtained.

The gas detecting and measuring device shown in FIG. 1 comprises a feed system for the gas or air to be tested, including a suction pump motor 1, and a suction pump 2 by which, through a connecting line 3, the gas or air to be examined is taken in through an indicator tube 4. A volume sensor 5 and a pressure sensor 6 are accommodated in the connecting line 3. The volume signal v of the volume sensor 5 is supplied to a characteristic generator 7 where it is converted into the desired pressure signal $p_s$ having a value corresponding to the characteristic. The characteristic is determined experimentally to reproduce the suction characteristic of a manually operated bellows pump employed in the calibration of the indicator tube. In accordance with the relation: desired value $P = f(v)$, this characteristic indicates the respective instantaneous desired value P through the entire measuring cycle, corresponding to the gas or air volume v already passed through the indicator tube. The desired value signal $p_s$ is applied, along with the actual-value signal $p_i$, to a subtractor 9. Through a speed governor 8 for suction pump motor 1, the differential signal from subtractor 9 controls the suction capacity of suction pump 2 in such a way that in connecting line 3, the actual pressure equals the desired pressure. This insures that the suction characteristic of the electromechanically driven gas detecting and measuring device coincides in any measuring phase with that of the manually operated bellows pump.

Figure 2:
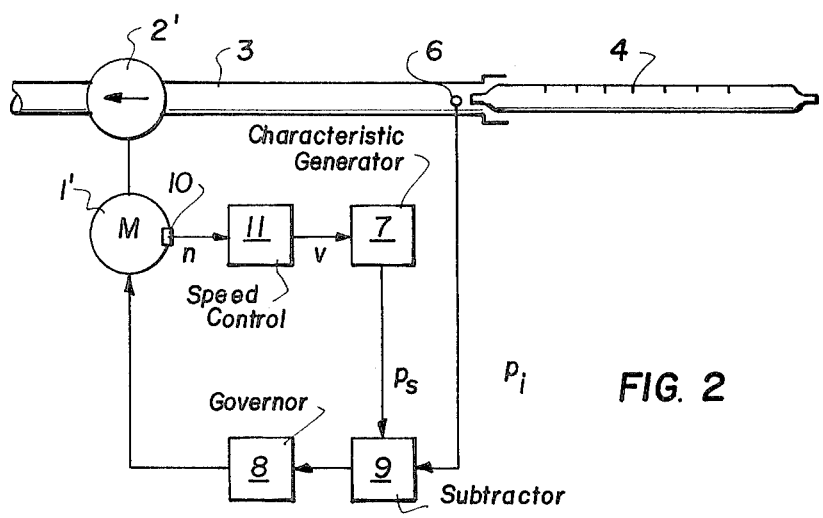
FIG. 2 is a view similar to FIG. 1 of another embodiment of the invention.

The gas detecting measuring device of FIG. 2 differs from the embodiment shown in FIG. 1 in that the volume signal is obtained in another way. The volume sensor 5 is omitted. To determine the gas or air volume taken therethrough, the number of revolutions n of suction pump motor 1' is utilized. The revolutions are picked up by means of a sensor 10 and converted into the volume signal v in a speed counter 11.

While specific embodiments of the invention have been shown and described in detail to illustrate the application of the principles of the invention, it will be understood that the invention may be embodied otherwise without departing from such principles.

What is claimed is:

1. A method of insuring reproducible results in testing gas of the type in which the gas is passed through a detection tube containing a measuring substance by a pump having an electrical motor with a speed governor connected thereto for regulating the pump speed, comprising the steps of passing the gas to be tested through the tube, sensing the gas volume being moved through the tube, converting the volume sensed to a desired pressure signal, sensing the actual pressure in the tube and forming an actual pressure signal, applying the desired pressure signal plus the actual pressure signal to a subtractor to form a differential pressure signal, and connecting the subtractor to the speed governor so that a differential signal from the subtractor controls the suction of the pump by equalizing the actual pressure with the desired pressure.

2. A method according to claim 1, wherein the step of sensing the gas volume which is taken in through the tube comprises determining the number of revolutions of the suction pump and converting the determined number of revolutions into a volume signal in a speed counter.

3. A gas detection and measuring device comprising a measuring vessel having a passage therethrough for the gas to be tested, pump means for drawing the test gas through said passage comprising a suction pump having an electrical motor for driving the suction pump and a speed governor connected to the electrical motor for regulating the speed thereof, a connecting line connected from said measuring vessel to said pump means, means for sensing a volume of the test gas passed to said connecting line, and generating a volume signal, a pressure sensor in said connecting line for generating an actual pressure signal, control means connected to said volume sensing means and said pressure sensor and to said governor for converting the volume signal to a desired pressure signal and applying a differential signal of the actual pressure signal and the desired pressure signal to the governor to control the pump so as to equalize the actual pressure signal with the desired pressure signal.

4. A gas detection and measuring device according to claim 3, wherein said control means includes a function generator, and wherein said volume sensing means includes means for detecting, the number of revolutions of the electrical motor operatively connected to said function generator, and for converting the number of revolutions to the volume signal and said function generator being operable to convert the volume signal into the desired pressure signal.

5. A gas detection and measuring device according to claim 4, wherein said control means includes subtractor means operatively connected to said function generator and said pressure sensor for generating the differential signal of the actual pressure signal and the desired pressure signal, said subtractor means being connected to said governor and being operable to apply the differential signal to said governor to thereby control the suction pump to effect the equalizing of the actual pressure signal with the desired pressure signal.

6. A gas detection and measuring device according to claim 5, wherein a sensor connected to said motor for sensing the number of revolutions and said detecting means includes a speed counter connected to said revolution and for generating the volume signal as a function of the number of revulutions.

7. A gas detection and measuring device according to claim 3, wherein said volume sensing means includes a volume sensor in said connecting line operable to form the volume signal and wherein said control means includes a function generator operatively connected to said volume sensor operable to form the desired pressure signal responsive to the volume signal and subtractor means for combining the desired pressure signal and the actual pressure signal to form a differential pressure signal, said substractor being connected to said governor, and said governor being operable to control the pump responsive to the differential signal.

* * * * *